United States Patent [19]

Kubler

[11] Patent Number: 5,529,692

[45] Date of Patent: Jun. 25, 1996

[54] METHOD AND APPARATUS FOR ANAEROBIC BIOLOGICAL HYDROLYSIS AND FOR SUBSEQUENT BIOMETHANIZATION

[75] Inventor: Hans Kubler, Munich, Germany

[73] Assignee: REA Gesellschaft fur Recycling von Energie und Abfall mbH, Munich, Germany

[21] Appl. No.: 406,763

[22] Filed: Mar. 17, 1995

Related U.S. Application Data

[63] Continuation of Ser. No. 46,971, Apr. 15, 1993, abandoned.

[30] Foreign Application Priority Data

Apr. 16, 1992 [DE] Germany .................. P 42 12 869.2
Aug. 6, 1992 [DE] Germany .................. P 42 26 087.6

[51] Int. Cl.⁶ .................................................. C02F 3/28
[52] U.S. Cl. .................................... 210/603; 210/743
[58] Field of Search .......................... 435/140; 210/603, 210/604, 605, 764, 614, 743, 85

[56] References Cited

U.S. PATENT DOCUMENTS

| | | | |
|---|---|---|---|
| 4,067,801 | 1/1978 | Ishila et al. | 210/764 X |
| 4,318,993 | 3/1982 | Ghosh et al. | |
| 4,551,250 | 11/1985 | Murper et al. | 210/603 |
| 4,579,654 | 4/1986 | Bremmer | 210/603 X |
| 4,597,872 | 7/1986 | Andersson et al. | 210/605 |
| 4,636,467 | 1/1987 | Chynoweth | 435/140 |
| 4,652,374 | 3/1987 | Cohen | 210/613 X |
| 4,781,836 | 11/1988 | Thiele et al. | |
| 4,849,108 | 7/1989 | de Wilde | 210/603 |

FOREIGN PATENT DOCUMENTS

| | | |
|---|---|---|
| 0048675 | 3/1982 | European Pat. Off. |
| 0351394A3 | 1/1990 | European Pat. Off. |
| WO92/13084 | 8/1982 | WIPO |

OTHER PUBLICATIONS

K. Buchholz et al., "Enzyme Production by Anaerobic Fermentation of Beet Pulp", Zucherind (1988) (English abstract is included.)

H. Rodriquez et al., "Characterization of the Cellulase Complex From Cellulomonas Grown on Bagasse Pith", Applied Microbiology & Biotechnology (1988).

J. E. Bailey et al., "Mixed Microbial Populations in Applications and Natural Systems", pp. 942–964 (1986).

T. Noike et al., "Characteristics of Carbohydrate Degradation and the Rate–Limiting Step in Anaerobic Digestion", Biotechnology and Bioengineering (1985).

G. Gonzalez et al., "A Kinetic Model for Pretreated Wheat Straw Saccharification by Cellulase", J. Chem. Tech. Biotechnol. (1989).

K. Buchholz et al., "Untersuchungen Zur Bildung Von Biogas Aus Rubenprebschnitzeln", Zucherindustrie (1986), pp. 837–844.

H. Gijzen et al., "High–Rate Two–Phase Process for the Anaerobic Degradation of Cellulose, Employing Rumen Microorganisms for an Efficient Acidogenesis", Biotechnology and Bioengineering (1988) pp. 418–425.

(List continued on next page.)

*Primary Examiner*—Frank Spear
*Attorney, Agent, or Firm*—Lowe, Price, LeBlanc & Becker

[57] ABSTRACT

A method for the biological processing of organic substances and more particularly for anaerobic biological hydrolysis for subsequent biomethanization, with pH value control, in the case of which the dissolved and/or undissolved organic substances supplied to a first reactor are at least subjected to slight acidification in such reactor, the major part of the undissolved, at least partly acidified organic substances taken from the first reactor are supplied to a second reactor for the performance of at least one solids hydrolysis step and the main part of the dissolved, at least partly acidified organic substances from the first reactor and from the second reactor are supplied to a third reactor for the performance of at least one methanization step.

41 Claims, 7 Drawing Sheets

OTHER PUBLICATIONS

Z. B. Zwart et al., "Anaerobic Digestion of a Cellulosic Fraction of Domestic Refuse by a Two–Phase Rumen–Derived Process", Biotechnology and Bioengineering (1988) pp. 719–724.

Hack et al., "A New Process for High Performance Digestion", International Symposium on Anaerobic Digestion of Solid Wastes, Venice 14–17.4.92.

S. Rettich, "Biogas und Kompost aus Kuchen–und Gartenabfallen—Pilotversuch in Rottweil", EF–Verlag, Berlin (1989).

Rodde et al., "Anaerobe Vergarund als Vorstufe zur Kompostierung", Informationgesprach 1989, ANS Infor–Band, vol. 16, p. 198.

H. J. Gijzen et al., "Anaerobic Digestion of Cellulose Fraction of Domestic Refuse by Means of Rumen Microorganisms", Biotechnology and Bioengineering (1988) pp. 749–755.

METHOD AND APPARATUS FOR ANAEROBIC BIOLOGICAL HYDROLYSIS AND FOR SUBSEQUENT BIOMETHANIZATION

This application is a continuation of application Ser. No. 08/046,971 filed Apr. 15, 1993, now abandoned.

BACKGROUND OF THE INVENTION

The present invention relates to a method for the biological processing of organic substances and more particularly for anaerobic biological hydrolysis for subsequent biomethanization and an apparatus for the performance of the method.

Biomethanization of complex organic materials is performed by the interplay of essentially three microorganism groups, that is to say:

1. Hydrolytic fermentative bacteria
2. Hydrogen producing acetogenic bacteria.
3. Methanogenic bacteria which consume hydrogen and acetate.

In this respect the products of the first group are processed by the second microorganism group and the products of the second group are processed by the third group. As a result the main products, methane and carbon dioxide, are produced from complex biopolymers.

Fermentative microorganisms preferentially utilize simple organic substances such as glucose or cellobiose in order to obtain energy, for such substances are dissolved and may therefore be directly resorbed. Under anaerobic conditions in such a case the products of fermentation are mainly organic acids or alcohols.

On the other hand complex organic substances such as for instance cellulose are not directly resorbed. They have to be firstly hydrolyzed to resorbable fragments. For this purpose hydrolytically active microorganisms excrete specific exoenzymes, which degrade the biopolymers. The products of such decomposition are then fermented in the anaerobic environment to give organic acids or alcohols.

Since the fermentation of dissolved substances is substantially more favorable for the microorganisms energetically, they only form hydrolytic exoenzymes in the absence of dissolved fermentable substances (Buchhoiz, K. and H.-J Arntz (1988) "Gewinnung von Enzymen durch anaerobe Fermentation yon Rübenpreβschnitzeln, Zuckerindustrie 113(1988), p. 204–208). This means that in the case of a substrate mixture of dissolved and undissolved substances it is firstly the dissolved substances which are substantially fermented, before the biopolymers are hydrolyzed and fermented.

In the case of an enrichment of the products in the medium there is an inhibition of the fermentation process. Such product-entailed inhibition is made more intense by the drop in the pH value due to the acids formed. It is more particularly in the case of pH values under 6 that owing to low dissociation of the organic acids formed a concentration inhibiting level is reached very quickly.

The activity of the hydrolytic enzymes is furthermore very much influenced by the pH value in the medium. Most hydrolytic enzymes of anaerobic microorganisms show maximum activity in a pH range of 6 to a little over 7(see Rodgriguez, H., Volfova, O. and Klyosov, A.: Characterization of the cellulose complex from Cellulomonas grown on bagasse pitch, App. Mircobiol. Biotechnolo. 28(1988), p, 394–397).

In order to counteract an enrichment of the acids formed and a drop in the pH value, it is necessary for the acids to be eliminated. Unlike the case of a single stage conduct of the method, in the case of which they are immediately methanized in the same reactor, in the case of multistage methods the acids produced in the hydrolysis and acidification stage have to be systematically removed and passed on to the methanization stage. This disadvantage of the multistage method is however countered by its higher efficiency (Bally, J. E. and Ollis, D. F.: Biochemical Engineering Fundamentals (McGraw-Hill, N.Y. 1977).

According to Noike (Noike, T., et al.: Characteristics of carbohydrate degradation and the rate-limiting step in anaerobic digestion, Biotechnology and Bioengineering, 27(1985), p. 1482–1489) in the case of the biomethanization of organic solids the anaerobic hydrolysis of the solids is the rate setting step. By setting to optimum conditions of the environment it is possible to increase the rate of conversion of the hydrolytic microorganism and consequently to accelerate the rate limiting degradation step. For many anaerobic hydrolytic microorganisms the optimum pH value is on the acid side.

For the biomethanization of the products of hydrolysis a neutral pH value is however more suitable. In the acidic range the material conversion of methan-ogenic populations decreases to a greater extent. As a result in the case of pH values, which are optimum for hydrolysis, the methanization of the products of hydrolysis is the rate limiting step. By separation of the two degradation steps by a dual-stage conduct of the method optimum basic conditions are obtained for both degradation steps.

In the case of continuous supply of complex substrates such as for instance mixtures of refuse, to the acidification stage, owing to non-interrupted supply of readily fermentable substances (which are generally in solution) hydrolysis of biopolymers is inhibited. Performance of the method in two stages with continuous feed of substrate and with acidification followed by hydrolysis suppresses such inhibition. The dissolved and readily fermentable substances are acidified in the first stage and only solids are added in the hydrolysis stage. Owing to this selection pressure a very active, hydrolytic population is established in the second stage with the result that the degradation of solids is increased.

Gonzales and co-workers (Gonzales, G., Caminal, G., De Mas, C., and Lopez-Santin, J.: A kinetic model for pretreated wheat straw saccharification by cellulase, J. Chem. Tech. Biotechnol. (1989) p. 275) showed that enzyme reactions for the degradation of cellulose may be described as Michaelis-Menten reactions. This means that high substrate concentrations have a favorable effect on hydrolysis. However with an increased concentration of solids the rheology in the reactor changes and owing to a limitation in transport the reaction rates decrease. Therefore for the hydrolysis of solids there is an optimum concentration thereof dependent on the respective substrate mixture.

However so far no such optimized methods have been described. In the case of the method described in the U.S. Pat. No. 4,781,836 for the biomethanization of organic substances with two processing stages the acidification of the dissolved components and the hydrolysis of the undissolved substance takes place in one and the same reactor in an environment which is not optimum for the processes performed therein. Furthermore the water circuits for the two reactors are completely separate from each other. This separation is produced by a combination of filters for solids/liquid separation and ion exchangers for the removal and transfer of the dissolved polar substances. Such a conduct of the method is unsuitable for the treatment of mixtures of complex substances containing solids, because suitable filters are either unable to deal with the acidified mixture or the filtrate contains too much solids to be dealt with by an ion exchanger. The European patent publication 89 890 162.4 A3 describes a method for increasing methane yield in the case of the fermentation of municipal organic waste using two separate stages, and two mixed fermentation stage involved therewith in a first and a second reactor, in the case of which respectively in the two reactors there is an acidification and methanization of the municipal organic waste. In the case of these methods as well the acidification of the dissolved components and the hydrolysis of the undissolved substances takes place in one and the same reactor under conditions which are not optimum.

Buchholz (1986), Gijzen and Zwart (Buchholz, K., Arntz, H.-J., Pelligrini A. and Stoppok E: Untersuchung zur Bildung von Biogas aus Rübenpreβschnitzeln, Zuckerindustrie 111(1986), p. 837–844; Gijzen, H. J. et al.: High-rate two-phase process for the anaerobic degradation of cellulose employing rumen microorganisms for an efficient acidogenesis, biotechnology and bioengineering 31(1988), p, 418–425; Zwart, K. B. et al.: Anaerobic digestion of a cellulosic fraction of domestic refuse by a two-phase rumen derived process, Biotechnology and Bioengineering 32(1988) p. 724–729) describe in their publications a two-stage process for the anaerobic fermentation of organic solids. In the case of this method as well the acidification of the dissolved components and the hydrolysis of the undissolved substances take place in one reactor.

This joint acidification and hydrolysis involves the disadvantage that the formation of the hydrolytic exoenzymes is suppressed until the dissolved and readily fermentable substances are completely acidified. In the case of a continuous supply of substrate an equilibrium concentration of the non-acidified and readily fermentable becomes established in the reactor dependent on the conversion rates. The result of this is that the formation of the exoenzymes and therefore the hydrolysis of solids is inhibited.

It is only with a discontinuous feed to the first reactor that in the case of this two-stage method it is possible to reduce the concentration of readily fermentable substances at times to such low values that satisfactory hydrolysis of the solids which are difficult to degrade may be ensured.

In the publication of Hack, P. J. F. M. and Brinkmann, J. A.: New Process for High Performance Digestion, International Symposium on Anaerobic Digestion of Solid Waste, Venice 14–17.4.92, a three-stage conduct of the process with the steps of acidification, hydrolysis and methanization is proposed, the individual method steps being performed in spatially separated reactors and in which the return of the material from the methanization stage is utilized for control of the pH value and the concentration of solids. In this method, which in the following is termed the PAQUES method, after mechanical pretreatment the solids are hydrolyzed and acidified in a reactor 1 (prethane reactor), the solids fractions susceptible of rapid degradation passing into solution. The resulting slurry is separated and most of the solids fraction is returned back to the prethane reactor for further hydrolysis. Only a minor quantity of the solids is transferred to the second reactor (RUDAD reactor).

In this second reactor it is more particularly ciliata and anaerobic fungi which serve to hydrolyse the solids fraction and cellulose and other fibrous compounds are somewhat acidified. The final products of this hydrolysis method are more particularly volatile fatty acids. The non-degradable solids are removed from the RUDAD reactor.

In a third stage and in a third reactor the liquid fraction from the reactor 1 and the hydrolysis products from the reactor 2 are methanized.

The anaerobic material from the third reactor is employed in the prethane reactor and in the RUDAD reactor for dilution and for pH value control.

This PAQUES method suffers from the disadvantage that the three parameters which are more particularly relevant for the process, that is to say control of the pH value, the concentration of solids in reactor 2 and the residence time of the solids in reactor 2 are only able to be changed interdependently so that an arbitrary or systematic modification of all three parameters for the control of the rate of hydrolysis of solids is substantially impaired. A further disadvantage of the PAQUES method is the return of the greater part of the solids feed into the reactor 1 (the prethane reactor) after separation. This conduct of the method among other things necessitates a separation of the feeds into two part feeds and consequently more complex equipment. A further disadvantage is the degradation of the solids by ciliata and anaerobic fungi in reactor 2. Because such microorganisms are normally not present in the solids so processed, it is necessary for the material to be introduced into the reactor 2 with a special inoculating sludge so that the method becomes more expensive.

SHORT SUMMARY OF THE INVENTION

Accordingly one object of the present invention is to develop a method constituting an advance over the prior art so as to be simpler and more efficient and more particularly to provide a control concept by means of which the pH value, the concentration of solids and the residence time of the solids may be set independently of each other.

A still further object of the invention is to provide apparatus which is suitable for the performance of the method in accordance with the invention.

In accordance with the invention there is the provision that the dissolved and/or undissolved organic substances supplied to a first reactor, are subjected in such reactor to at least a partial acidification step, the greater part of the undissolved and at least partly acidified organic substances taken from the first reactor are supplied to a second reactor for the performance of at least one solids hydrolysis step and the greater part of the dissolved and at least partly acidified organic substances from the first and second reactors go to a third reactor for the performance of at least one methanization step.

For improved separation of the dissolved organic substances from the undissolved ones in a separate method step the dissolved and undissolved organic substances from the first reactor 1 are subjected to separation into a solids fraction with the undissolved organic substances and a liquid fraction with the dissolved organic substances.

The advantage of a separate acidification and hydrolysis stage is that, as dictated by the requirements of the method, only substantially acidified material (that is to say only a minor quantity of the readily fermentable substances) is supplied to the hydrolysis stage and therefore even in the case of continuous supply of the organic substances uninhibited solids hydrolysis is ensured.

In accordance with the invention the greater part of the solids feed from the reactor 1 is transferred into the reactor 2. In the PAQUES method however, unlike the method in accordance with the invention, the solids feed from the first separating device 4 (FFT4) is mainly returned to the reactor 1. Only one solids feed is returned to the reactor 2. The transfer of flowing feeds bearing solids is difficult in practice, more particularly if a solids feed—as in the PAQUES method — has to be separated into two part flows or feeds. In order to ensure proper operation it is then necessary for the return to reactor 1 to take place separately from the supply of solids to reactor 2. To make good the loss of water and to keep the contents of the reactor in a mixable and pumpable condition it is necessary for water, that is to say material from the methane reactor, to be additionally supplied to the reactor 1. These measures necessitate an apparatus which is larger in size and more complicated than that necessary in the method of the invention.

It will be seen from table 1 that for instance for solids hydrolysis in the case of biowaste a pH value of 6.4 is optimum. As regards the stability of the pH value for solids hydrolysis the pH value range of 6.0 to 6.8 is however relatively critical.

TABLE 1

| Acidification reactor 1 pH | Solids hydrolysis reactor 2 | | |
|---|---|---|---|
| | SRT [d] | pH | Degradation of organic solids supplied [%] |
| 4.5–6.0 | [d] | | [%] |
| 4.5–6.0 | 3 | 5.5 | 44 |
| | 3 | 6.4 | 70 |
| | 3 | 6.7 | 38 |

SRT stands for solids retention time and here indicates the solids residence time.

SRT stands for solids retention time and here indicates the solids residence time.

Table 2 will be seen to indicate a similar behavior in the case of the hydrolysis of cellulose in a manner dependent on the pH value during solids hydrolysis.

TABLE 2

| Solids hydrolysis reactor 2 | | |
|---|---|---|
| SRT [d] | pH | Degradation of cellulose supplied [%] |
| 3 | 5.5 | 41 |
| 3 | 6.4 | 44 |
| 3 | 6.7 | 49 |

Table 3 presents a comparison between different manners of performing the method for biomethanization of organic solids from biowaste as regards the degradation of organic dry mass, which clearly indicates the advantages of the method in accordance with the invention with its more rapid and substantially more complete degradation of the organic dry mass feed.

TABLE 3

| Method | Source | Residence time [d] | Degradation of supplied organic dry mass [%] |
|---|---|---|---|
| Single stage | Rettich | 12 | 42 |
| Two stage | Rodde | 12 | 50 |
| Multistage with pH | Investigations | 9 | 74 |

TABLE 3-continued

| Method | Source | Residence time [d] | Degradation of supplied organic dry mass [%] |
|---|---|---|---|
| controlled solids hydrolysis | of inventors | | |

See in this respect: Rettich, S: Biogas und Kompost aus Küchen- und Gartenabfällen. Pilotversuch in Rottweil, in Thomé-Kozmiensky: Biogas-Anaerobtechnik in der Abfallwirtschaft, published by EF-Verlag, Berlin 1989, and Rodde, Christian and Westphal, W.: Anaerobe Vergärung als Vorstufe zur Kompostierung, 42. Informationgespräch 1989, ANS Info-Band, vol 16, p. 198.

For control to maintain this critical pH value in accordance with the invention dissolved and undissolved organic substances are directly taken from the first reactor and more particularly introduced into the second reactor for lowering the pH value; independently therefrom the pH value may be affected in the second reactor and more particularly increased if dissolved and undissolved organic substances are taken from the second reactor and of such substances at least a part of the dissolved organic substances is are supplied to the third reactor, the remaining part being returned to the reactor 2.

Owing to the absorption of a part of the carbon dioxide formed during methanization the material from the third reactor has a corresponding buffer capacity, which may be utilized by return to the hydrolysis stage in the second reactor for (a) increasing pH value, makes a contribution to increasing the buffer capacity in the overall system and for (b) controlling the ratio between dissolved and undissolved substances and of the solids content in the second reactor. Tests performed by the inventors showed that the acid capacity of this feed was approximately 180 mval/l. In order to reduce the pH value from for instance 6.7 to 6.3 24 mval/l were necessary.

If in the case of a substrate-dependent reduction of the hydrolysis rate there is a slight rise in the pH value, this will in this range lead to a considerable increase in the methanization rate of biozoenosis in the hydrolysis sector. As a result there is a sudden increase in the acid consumption and the pH value continues to increase. As a consequence of this the formation of methane increases even more and there is a further increase in acid consumption.

Owing to the enhanced methanization rate and the high buffer capacity in the hydrolysis reactor therefore large quantities of acids are necessary for lowering the pH value. If in the case of a two stage system in this situation the current feed does not contain sufficient acid or readily fermentable substance, it is impossible for the pH value to be further stabilized and it will drift off into the neutral range. In the neutral range the pH value will be very stable, because the hydrolysis of solids constitutes the rate determining factor and consequently all the acids produced are immediately methanized.

A lowering of the pH value in this condition of the process is only made possible by the addition of large quantities of acid. If no additional acid is to be fed into the system, for pH value correction it is necessary to have a large quantity of substantially acidified substrate available. This is in principle only the case with the three stage system described here.

If however the input is heavily acidified so that there would be sufficient acid for pH value control in a two stage system, the continuously high supply of acid to the hydrolysis reactor will also entail a correspondingly substantial removal of acid. Because in this case the acid concentration in the feed is higher than in the hydrolysis reactor, in the case of a direct supply of the input into the hydrolysis reactor, as described by Buchholz, Gijzen and Zwart (loc. cit.) with previous dilution of the input, the input is firstly diluted. This means that in comparison with the three stage method described here for the removal of the same quantity of acid for methanization more substrate has to be pumped for solids/liquid separation. Accordingly such plant is to be made larger in size.

Furthermore in the case of the method in accordance with the invention it is possible to control the water content in the system by removing excess water from the third reactor.

The method in accordance with the invention therefore renders possible an optimum setting of the conditions for solids hydrolysis in reactor 2, and more particularly an independent setting of the pH value, the solids concentration and the solids residence time in reactor 2. FIG. 3 in conjunction with FIG. 1 represents a diagram of regulation for the pH value in detail.

The pH value is controlled by changing the flows through the servo elements, (for example pumps) P11, P12 and P13. The pH value is best measured directly in reactor 2 (pH R2). If this is not practical, measurement of the pH value in the line 13 (pH L13) is possible. In this case however a certain recirculation current (13) is necessary. This flow rate will determine the minimum flow through P13.

The solids concentration in the hydrolysis reactor is controlled by a suitable ratio between the returned methanization output material (22), which is controlled via the pumping rate of P22, to the liquid phase (20) produced and measured with flow the rate measuring means 20.

The residence time of the solids in the solids hydrolysis means (reactor 2) is determined on the basis of the rate of supply of acidified mixture (sum of 11 and 12).

For lowering the pH value the first measure is the reduction of return of the reactor content to FFT4 (13). This is achieved by a reduction in the pumping rate of P13. Simultaneously the return of methanized output material to the reactor 2 (22) is also reduced in accordance with the predetermined ratio. Therefore the solids content in the reactor 2 may be held constant and the reduction in the pH value is increased.

If the pumping rate of P13 is at a minimum or zero and a further reduction in the pH value is necessary, acidified mixture (12) is supplied directly to the reactor 2 and (11) its pH value reduced. For this purpose the pumping rate of P12 is increased and the rate of P11 is correspondingly reduced. By adaptation of the pumping rate of P22 to suit the liquid phase (F20) produced in accordance with the predetermined ratio the solids content in the reactor 2 is maintained constant.

For increasing the pH value firstly (11) is increased and (12) correspondingly reduced. For this purpose the pumping rate of P11 is increased and that of P12 correspondingly choked back. In order to keep the concentration of solids in the reactor 2 constant simultaneously the supply of methanization output material is correspondingly increased. Therefore the increase in the pH value is additionally favored.

If the complete supply of the acidified mixture via (11) is not sufficient, (13) and (22) is increased. For this purpose the pumping rate of P13 is increased and the return of the methanization output material is adapted to the quantity of filtrate (F20). The concentration of solids in reactor 2 is consequently maintained constant.

The concentration of solids in reactor 2 may be changed by adapting the ratio between the returned methanization output material and the liquid phased produced. Then the pumping rates of P11, P12 and P13 are suitably set to ensure the intended pH value in reactor 2.

In the case of the operations described for control of the pH value and the concentration of solids in reactor 2 it is possible for the supplied quantity of acidified mixture (sum of 11 and 12) to be maintained constant and thus the solids residence time in reactor 2 is changed.

Such a control of the pH value to be independent of the solids concentration and the solids residence time in reactor 2 is impossible in the PAQUES method.

A reduction in the pH value in the RUDAD in the PAQUES method is only made possible by the following three measures:

1. An increase in the supply of solids (increase in load).
2. Reduction in the return of the methanization output material.
3. Modification of the separating effect in the solids/liquid separation stage.

Each of the three measures however means that less favorable conditions are produced for the solids hydrolysis.

An increase in the supply of solids means that there has to be an increase as well in the supply of methanization output material in order to keep the solids concentration constant. This means that there is a greater reduction of the residence time in reactor 2. Shorter solids residence times lead to a smaller degree of degradation (FIG. 4). Furthermore the increase in the returned quantity of methanization output material counteracts or outweighs a drop in the pH value.

If the return of the methanization output material is reduced and the supply of solids is kept constant or increased, it is possible by reduction of the recirculation in the RUDAD reactor to prevent an increase in the solids. If the recirculation is zero and if for reduction of the pH value the return of the methanization output material has to be reduced still more, the solids concentration in reactor 2 will increase. This may lead to inhibition of the solids hydrolysis by limiting transport or to overloading and damage to the plant.

A systematic modification of the separating effect in the case of solids/liquid renders the plant complex. A further point to be considered is that owing to frequent changes in the separation properties of the mixed waste to be processed frequently determination of the separating effect during the separation of solids from liquids is necessary. Since for the present flows of material, owing to their composition no on-line determination of the separation effect is possible, such determination has to be performed by analysis in the lab. Therefore no prompt modification of control is possible with this parameter.

In order to increase the pH value in reactor 2 there are two reaction possibilities available for the Paques method which as well have disadvantageous effects:

1. Increasing the return of methanization output material.
2. Reduction the supply of solids.

An increase in the return rate for the methanization output material, given a constant supply of solids and a simultaneous increase in the recirculation in the RUDAD reactor, does not lead to an influence on the solids concentration and or on the solids residence time.

A reduction in the supply of solids lowers the process throughput.

Owing to the interrelationships in the PAQUES method it will be apparent that it is impossible to control in reactor 2 (the RUDAD reactor) the parameters in the form of the pH value, the solids concentration and the solids residence time independently of each other. As explained however a systematic or independent variation of all three parameters is decisive as regards the rate of hydrolysis of the solids.

On the other hand the method in accordance with the invention is superior to the prior art as regards the control of the pH value and the concentration of solids in reactor 2. Using such a control scheme it is possible for the pH value, the solids concentration and the residence time to be set independently of each other.

By way of a conclusion there are following parameters and control quantities in solids hydrolysis:

| Parameter | Control quantity |
| --- | --- |
| Residence time of solids | Amount to be supplied of acidified mixture (sum of 11 and 12) + removed material |
| Solids concentration in solids hydrolysis stage | Ratio between the methanization output material (22) to be returned and the liquid phase produced (20) + feed 11 + 12 |
| pH value in solids hydrolysis | Rates of pumping at the servo members P11, P12 and P13. |

A comparison between the parameters relevant for the process in the PAQUES method in accordance with prior art and the method in accordance with the invention may be presented as follows.

| Process relevant parameters | PAQUES | Method in accordance with the invention |
| --- | --- | --- |
| A. pH value control | affects B. and C. | independent of B. and C. |
| B. solids concentration in reactor 2 | is affected by A. + C. | may be maintained constant independent from A. and C. |
| C. residence time of solids in reactor 2 | is dependent on input of solids | is dependent on input of solids |

In the RUDAD reactor ciliata and anaerobic fungi play a significant role in the degradation of solids (Gijzen, H. J. et al., Anaerobic digestion of Cellulose Fraction of domestic refuse by means of rumen microorganisms, Biotechnology and Bioengineering 32(1988), p. 749–755). Since the same are normally not present in the solids to be processed, this method necessitates starting up reactor 2 with a special inoculating sludge, something unnecessary in the method in accordance with the invention. In the reactor 2 suitable microorganisms are selected from the microorganisms contained in the supplied solids. This is performed by suitable adjustment of the pH value and of the solids residence time (duration of the time for the generation of the said desired microorganisms).

The yield in the production of biogas and more particularly methane gas can be increased if in the second reactor in addition to the solids hydrolysis methanization is performed and if biogas, more particularly methane gas, is taken from the second and third reactors. It is in this manner that the volumetric load in the third reactor may be lowered and therefore the degree of degradation in the third reactor may be increased.

In the following table 4 the composition of the gas from the hydrolysis of solids and from the methanization is given in % by volume.

TABLE 4

|  | pH value | $CO_2$ | $CH_4$ |
| --- | --- | --- | --- |
| Solids hydrolysis | 5.5–7.7 | 25–80 | 19–74 |
|  | 5.9 |  | 20 |
|  | 6.4 |  | 26 |
|  | 7.0 |  | 47 |
|  | 7.4 |  | 59 |
| Methanization | — | 19–33 | 66–80 |

The advantages of this method in accordance with the invention are able to be realized using the apparatus as claimed in any one of the claims 23 through 41.

The invention will now be described in the following with reference to the accompanying drawings in detail.

LIST OF THE SEVERAL VIEWS OF THE FIGURES.

Figure 1:
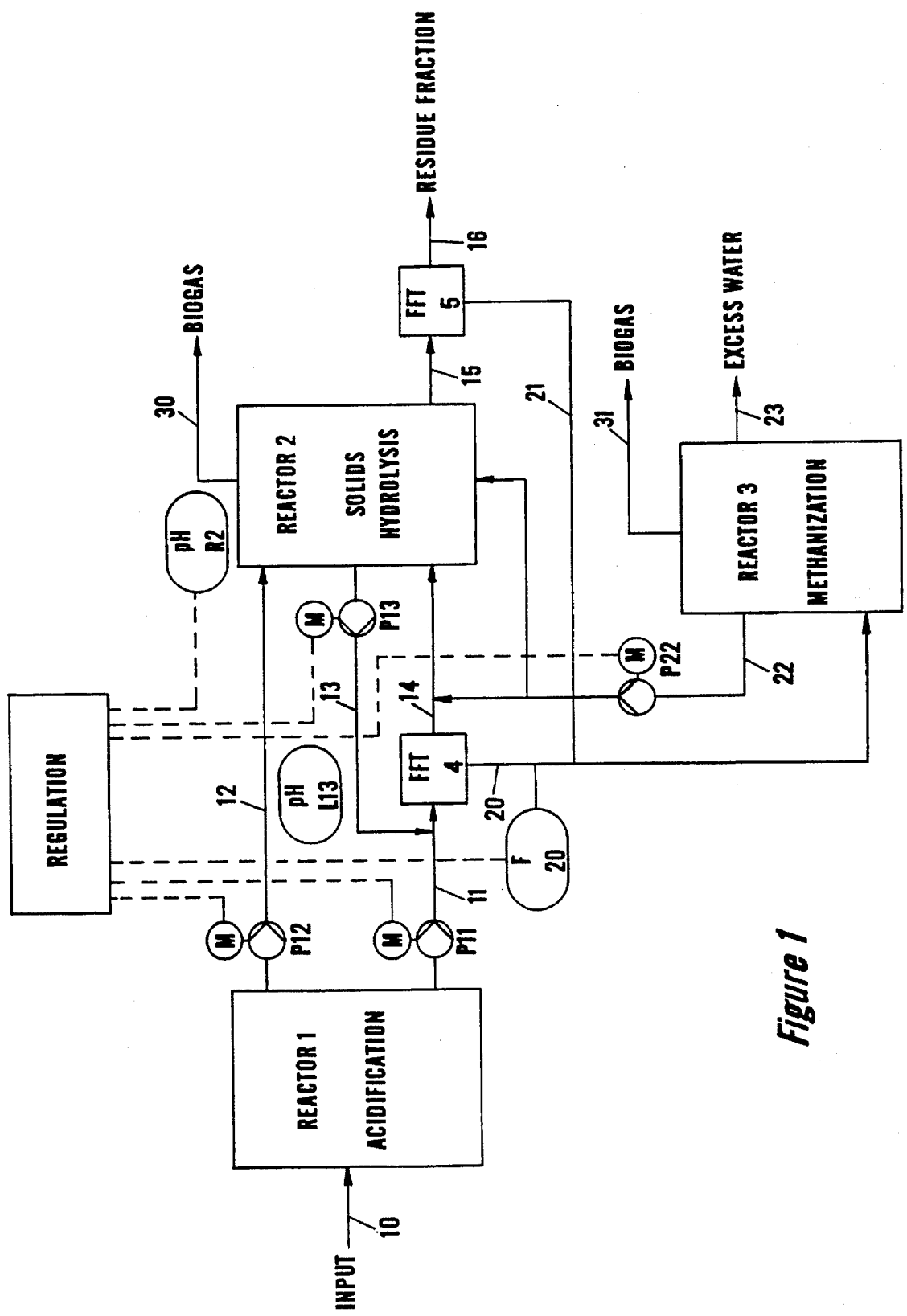
FIG. 1 is a block diagram of an apparatus for performing the method in the case of continuous charging of the solids hydrolysis stage, with pH value control.

DETAILED ACCOUNT OF APPARATUS USED IN THE INVENTION.

The following firstly provides a detailed description of the apparatus.

Essentially the apparatus comprises a first reactor 1 for the acidification of the organic substances, a second reactor 2 at least for the solids hydrolysis of the slightly acidified undissolved organic substances and a reactor 3 for the methanization of the dissolved organic substances.

There is an inlet or input 10 arranged on the reactor 1, through which the reactor is able to be charged with the organic substances to be processed.

By means of a communicating element 11, which may consist of a duct, a channel or the like, the reactor 1 is connected with a separating device 4, in which in a suitable and known manner dissolved and undissolved substances are able to be separated and the dissolved substances are able to be removed as a liquid fraction via a communicating element 20 and the undissolved substances are able to be removed via a communicating element 14.

The element 14 is connected with the reactor 2 and the element 20 is connected with the reactor 3 so that dissolved substances removed from the reactor 1 are able to be supplied to the reactor 3 and undissolved substances removed from the reactor 1 are able to be supplied to the reactor 2.

Via a further communicating element 12 the reactor 1 is directly connected with the reactor 2 so that owing to this substances located in the reactor 1 are able to be directly fed to the reactor 2. By means of a communicating element 13 the reactor 2 is connected with the element 11 with the result that dissolved and undissolved substances are able to be removed from the reactor 2 and able to be fed into the separating device 4, the undissolved organic substances being able to be supplied to the reactor 3. In contradistinction to the apparatus for performing the PAQUES method the apparatus in accordance with the invention has no duct for the return of the solids into the reactor 1.

The reactor 3 is connected via a further communicating element 22 with the reactor 2 directly or alternatively and additionally with the element 14 with the result that substances present in the reactor 3 are able to be fed into the reactor 2.

The reactor 3 has an outlet 23 suitable for the controlled removal of water.

The reactor 3 and the reactor 2 as well are provided with outlets for the removal of gas, more particularly biogas such as methane gas, same having suitable connections for further ducts for such removal.

In a first working embodiment, which is preferably utilized in the case of continuous charging of the solids hydrolysis stage, the reactor 2 is connected by means of a communicating element 15 with a separating device 5 (FFF5) for the separation of dissolved and undissolved materials to give a solids fraction and a liquid fraction. The separation device is connected by means of a further communicating element 21 with the element 20 so that dissolved substances removed from the reactor 2 are able to be supplied to the reactor 3.

Via an outlet 16 provided on the separating device 5 or via a communicating element 16 residues are able to be removed from the separating device 5.

In the case of a second working embodiment, which is preferably utilized in the case of discontinuous charging of the solids hydrolysis stage, the element 14 is connected with a communicating element 16 with the result that the solids fraction obtained by the separating device 4 may be removed via the element 16 as a residue. The control of the pH value in the case of discontinuous charging is indicated in detail in FIG. 2.

DESCRIPTION OF METHOD IN ACCORDANCE WITH INVENTION IN DETAIL

Via the input 10 dissolved and/or undissolved organic substances are supplied to the first reactor 1 and acidified.

The at least somewhat acidified organic substances are taken from the reactor 1 and supplied via the element 11 to a separating device, in which they are separated into a solids fraction which essentially contains the undissolved organic substances, and a liquid fraction, which essentially contains the dissolved organic substances.

The liquid fraction is supplied via the element 20 to the reactor 3, whereas the solids fraction is supplied via the element 14 to the reactor 2.

In the reactor 2 the undissolved organic substances are subjected to solids hydrolysis. In addition to this the dissolved organic substances formed during solids hydrolysis may be subjected to methanization.

In the reactor 3 there is a methanization of the organic substances present therein.

In accordance with a further development of the method organic substances are taken from the reactor 1 via the element 12 and supplied to the reactor 2 for controlling the pH value therein, and more particularly for reducing the pH value.

Via the element 13, in accordance with a further working embodiment, organic substances are removed from the reactor 2 and fed through a part of the element 11 to the separating device 4, by means of which the liquid fraction produced therefrom is fed to the reactor 3 through the element 20 and the solids fraction obtained by means of the separating device is passed via the element 14 to the reactor 2. This means that owing to deposition of the dissolved organic substances there is as a rule an increase in the pH value in the reactor 2, something which is utilized for the control of the pH value in the reactor 2.

The solids content in the reactor 2 is controlled by supplying a low-solids feed from the reactor 3 via the element 22 to the reactor 2. Furthermore in this case the buffer capacity of the substances present in the reactor 2 is increased.

Owing to the removal of excess water from the reactor 3 via the communicating element 23 it is possible for the ration between the water supplied to the first reactor 1 with the organic substances and the water removed from the third reactor to be allowed for or made good with the result that the water level in the overall system, more particularly of the reactors 2 and 3, can be controlled.

In accordance with a first further working embodiment the reactor 2 is continuously charged and organic substances are continuously removed from the same via the element 15, which organic substances are separated in the separating device 5 into a solids fraction and a liquid fraction.

The solids fraction is removed from the separating device 5 via the element 16 as residue. The liquid fraction is supplied to the reactor 3 via the element 21 and a part of the element 20.

In a second working embodiment the reactor 2 is discontinuously charged; in this case the removal, which is as well discontinuous, of residue is performed via a further element 16 connected with the element 14.

The biogases produced in the method are in the working embodiment taken from the reactor 2 and the reactor 3 via outlets 30 and 31.

In what follows a further overview of the most significant features of the method in accordance with the invention will be presented.

The method in accordance with the invention provides an improvement in the anaerobic biological hydrolysis and biomethanization of complex organic substances such as for instance biopolymers.

The inhibition of solids hydrolysis in the hydrolysis stage in the case of the continuous supply of complex substrates with readily fermentable components is prevented in accordance with the invention by a preceding method stage (acidification stage). Because of this there is a greater degradation of organic solids. This firstly leads to a higher yield of biogas and secondly, owing to reduced production of solid residues, leads to lower disposal costs.

Owing to the control of the pH value and of the solids concentration in the hydrolysis reactor the biological hydrolysis of the solids is accelerated. Given the same residence times this leads to a greater degradation or, for the same degradation it leads to a smaller reactor size owing to the shorter residence times.

Furthermore it is possible, in the case of having the same continuous charging of the system to set an optimum pH value in the hydrolysis reactor. Therefore no modification in the charging rate is necessary for control of the pH value.

In the case of the biomethanization of solids control of the pH value is frequently uneconomic owing to the additional requirement for acids or alkalis. In this method products produced in the process are employed exclusively for pH value control, something which makes the process more economic.

If no alkali is utilized, reduction in the pH value is normally obtained by reduction of the reactor load or charge. This means that there is a reduction in the throughput of the method. In order to maintain a minimum throughput it is therefore necessary to over-dimension the biological stage. Control of the pH value can be utilized to counteract a drop in the pH value without reduction of the throughput and hence it is possible to make savings as regards freedom of plant design.

The method makes use of separate reactors for acidification, hydrolysis and methanization. The organic acids formed during acidification and hydrolysis are separated in a solids/liquid separating unit and fed into the methane reactor. The material from such hydrolysis reactor is dewatered, the liquid phase is supplied to the methane reactor and the solids are let off. A part of the methanization reactor output material is fed back to the hydrolysis reactor.

In the aqueous phase the organic materials are present with a dry residue of 1 to 25% by weight as a mixture of dissolved and undissolved substances. The mixture (10) is fed back to the reactor 1. This container serves for the storage and, to the extent that the dissolved organic substances are not already spontaneously acidified, for further fermentation of the anaerobically degradable dissolved substances. If sufficient fermentation microorganisms are not introduced with the substrate mixture into the acidification reactor, the latter may be inoculated with suitable bacteria and operated in a suitable manner so that such bacteria proliferate to a sufficient degree and are not washed out. Owing to the substantial fermentation of the dissolved components of the input a low pH value becomes established in reactor 1.

The acidified mixture is passed from the reactor 1 into the reactor 2 for hydrolysis of the solids. Since, as for instance in the case of biowaste, its pH value is too low (see table 1) for increasing the pH value in the reactor 2 the mixture is dewatered (11) by means of a solids/liquid separating stage (FFT4) to a level, which is optimum for solids hydrolysis. This means that the acids formed during fermentation are removed with the liquid phase (20) to the reactor 3. The dewatered solids fraction (14) is supplied to the reactor 2. By return of the output material from reactor 3 (22) buffer capacity is made available in the hydrolysis reactor. The return of the methanization reactor output material may be either direct or together with the solids fraction (14).

Owing to the return of the methanization output material methanogenic microorganisms are constantly supplied to the reactor for solids hydrolysis. Therefore, in addition to a hydrolytic biozoenosis, a methanogenic biozoenosis becomes established in the reactor 2, which methanogenic biozoenosis directly converts the acids formed during hydrolysis of solids to biogas (30). The activity thereof is significantly dependent on the pH value of the hydrolysis stage. If the degradation of the acids formed by the methanogenic microorganisms corresponds to the rate of production of acids by the hydrolytic microorganisms, the pH value in the reactor will keep constant.

If in this conduct of the method owing to an excessively high activity of the methanogenic microorganisms the pH value in the reactor 2 increases to a level which is too great for optimum solids hydrolysis, it is possible to directly add the acidified mixture (12) to reduce the pH value back to an optimum level.

If on the other hand with a complete addition of the acidified mixture from reactor 1 to the solids/liquid separation stage 4 the pH value in reactor 2 sinks excessively, it is possible to use recirculation of the contents of reactor 2 (13) to remove the acids formed. The replacement of the removed liquid phase by methanization output material (22) increases the buffer capacity and favors the direct degradation of the acids formed during solids hydrolysis (in reactor 2).

Removal from the solids hydrolysis stage (15) takes place in a manner dependent on the necessary solids residence time in reactor 2. It is supplied to the solids/liquid separation stage 5 (FFT) and dewatered. The solids (16) are drawn off and the liquid phase (21) is subjected to methanization (in reactor 3).

During methanization the dissolved substances supplied with the liquid phases from the solids/liquid separation stage (20 and 21) are converted into biogas (31). A part of the carbon dioxide produced is then absorbed in the liquid phase and for this reason the methanization output material has a substantial carbonate buffer capacity which is utilized for increasing the pH value in the solids hydrolysis.

If with the input (10) more water is introduced than residues (16) and biogas (30 and 31) are removed with the flows, a part of the methanization output material is to be drawn off as excess water (23). If on the other hand the water content of the input is too low, it will have to be raised to a higher level in order to make good the water losses with the flows 16, 30 and 31.

Modification of the ratio between returned methanization output material (22) to removed liquid phase (20) can be utilized to control the solids concentration in solids hydrolysis. If for the mixture to be treated in the hydrolysis reactor the respectively optimum solids concentration is set, this will be responsible for an increase in the reaction rate. Accordingly it is possible for the residence time and consequently the reactor volume for the hydrolysis stage to be reduced.

If the acidification of the readily fermentable substances is not complete in the acidification stage, a part of such substances is introduced with the solids feed (14) into the solids hydrolysis stage. This means that hydrolysis of the solids in reactor 2 may be inhibited. Such inhibition can be counteracted by discontinuous charging into the hydrolysis stage. In this respect it is necessary for the charging intervals to be made so long that in this time the readily fermentable substances introduced into the reactor 2 are substantially acidified and thereafter there is sufficient time available for a substantial hydrolysis.

By discontinuous charging of the solids hydrolysis stage (in reactor 2) from the acidification stage (in reactor 1) it is possible to save having the second device for solids/liquid separation (FFT5). In this case the removal of the output from the solids hydrolysis stage is via FFT1.

In this case the reactor I functions not only for acidification but furthermore for storage of the input. The discontinuous operation of the solids hydrolysis stage takes place in three phases.

In phase 1 the solids hydrolysis stage is charged with a predetermined quantity of acidified mixture (11, 12). The distribution to 11 or 12 is performed in this case in accordance with the pH value to be set for reactor 2. In accordance with a predetermined ratio a part of the liquid phase 20 removed for methanization is replaced by return of the methanization output material.

If the pH value increases above the desired value, the fraction of the directly supplied quantity of acidified mixture (12) is increased. This means that the pH value in reactor 2 goes down.

If all the acidified mixture is supplied via the solids/liquid separation stage (FFT) to reactor 2 and the pH value in the solids hydrolysis stage is too low, in a phase 2 the solids hydrolysis content is recirculated via the solids/liquid separation stage and a part of the liquid phase produced (20) is replaced by methanization output material. This means that there is an increase in the pH value in reactor 2 to the predetermined desired value. The phase 2 may either take place after phase 1 or simultaneously therewith.

Discharge from reactor 2 takes place in phase 3, which in time follows phases 1 and 2. In this respect the dewatered solids are not returned, as in phase 2, to the solids hydrolysis stage, but drawn off from the process.

The decisive role played by the pH value of the reactor 2 for the result of solids hydrolysis can be seen from the said table 1. These test results are obtained on processing source-separated residential biowaste in a semi-scale pilot plant, with which the process as described herein was conducted. Modifications in the pH value of 0.3 units even lead to a significant reduction in solids hydrolysis.

In the reactor 1 it was not possible for such conditions to be adhered to owing to uncontrolled acidification. The pH value is substantially under the optimum for solids hydrolysis and if there are variations of 1.5 units the necessary constancy of the pH value is not possible.

The optimum pH value in solids hydrolysis is significantly dependent on the composition of the substances to be hydrolyzed. If for a "biowaste" mixture the optimum pH value is 6.4(table 1), the cellulose fraction of the biowaste is more readily hydrolyzed at a pH value of 6.9(table 2).

A comparison between the results with the manner of performing the method of processing biowaste (table 3) with results reported in the literature on anaerobic fermentation will make clear the superiority of the multistage method in accordance with the invention involving pH value-controlled hydrolysis of solids. With a shorter residence time a higher degradation rate is obtained. Since in the literature the bases of the residence times are different, for table 3 the quoted residence times have been converted for a uniform basis.

The plant used for the performance of the method is to be adapted to suit the specific properties of the substrates to be processed.

In accordance with the rheology, the degree of acidification and the acidification kinetics of the input (10) the reactor can be designed as a reactor with means for thorough mixing or as a simple container. The reactor 2 is to be designed either as a reactor with means for thorough mixing or as a cascade of a plurality of reactors or as a plug-flow reactor. As a reactor 3 different types have been tested. In this respect stationary bed reactors produced better result than UASB reactors and contact sludge reactors. Furthermore a plurality of reactors in cascade is possible. The reactor 2 and the reactor 3 are both made gas tight in order to ensure a quantitative capture of the biogas produced. Table 4 gives details of the gas composition of the two reactors. The methane level in reactor 2 is considerably affected by the pH value. The lower the pH value the lower the methane content.

In accordance with the invention it is therefore preferably possible to have a cascade, that is to say a plurality of such hydrolysis or methane reactors in lieu of a respective individual hydrolysis or methane reactor.

All three reactors may be operated in the mesophilic or furthermore in the thermophilic temperature range. For reactor 1 the psychrophilic temperature range is also possible.

Dependent on the particle size distribution and the separation behavior of the solids it is possible to utilize sieves, filters, filter presses, screw presses or decanters for solids/liquid separation of 11, 13+15.

The measurement of the pH value in the solids hydrolysis stage is performed either in reactor 2 or in the duct leading to the solids/liquid separation stage (FFT4, 14). To provide better accessibility a duct is to be preferred to a reactor. Metering of the acidified mixture (11, 12) into the reactor 2 and to the solids/liquid separation stage 4 is performed by means of pumps. The pumping rates of such pumps are controlled in accordance with the pH value in reactor 2. If its pH value is to be lowered, the pumping rate in 11 is to be reduced and the pumping rate along 12 is to be increased a corresponding amount. In order to raise the pH value in reactor 2 as a first measure the pumping rate in 11 is increased and correspondingly reduced in 12. If the acidified mixture is completely supplied to solids/liquid separation stage 4 and the pH value in reactor 2 is still too low, the pumping rate in 13 will be increased.

The solids phase of the solids/liquid separation stage (FFT4) passes to the solids hydrolysis stage either under gravity (for this purpose solids/liquid separation stage 4 must be at a higher level than the reactor 2) or by means of a pump means, as for instance a solids pump. In order to mitigate this pumping problem it is possible for the methanization output material (22), which is to be recirculated, to be mixed directly with the solids phase and then pumped into reactor 2.

The solids content in reactor 2 is set by a corresponding volumetric ratio between returned methanization output material (22) to draw off liquid phase. By means of flow rate measurement in 20 the drawn off volume is ascertained and the rate of pumping in 22 is adjusted in accordance with the empirically ascertained volumetric ratio.

Figure 6:
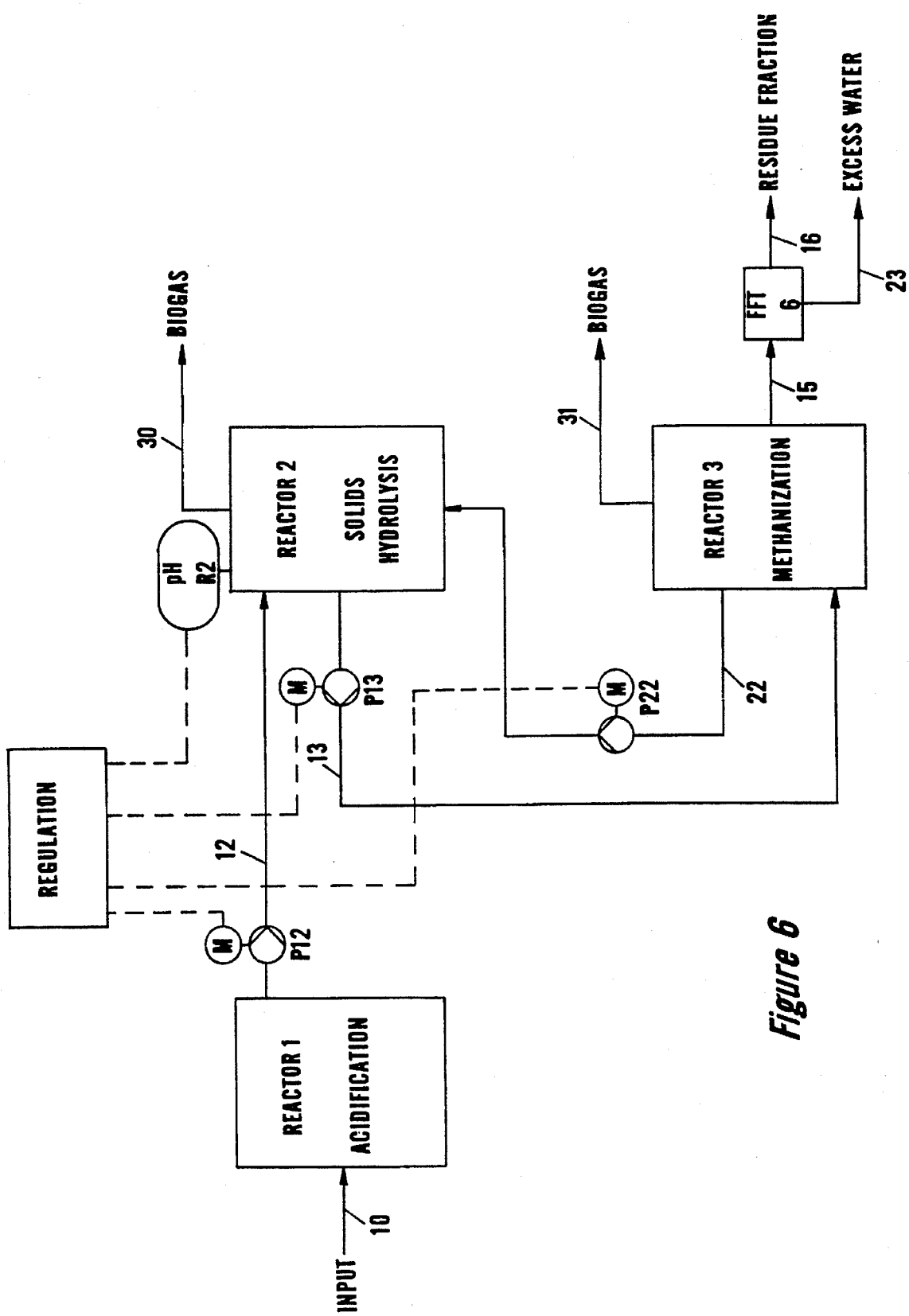
FIG. 6 is a block diagram of the apparatus in accordance with the invention with a simplified conduct of the method.
Figure 7:
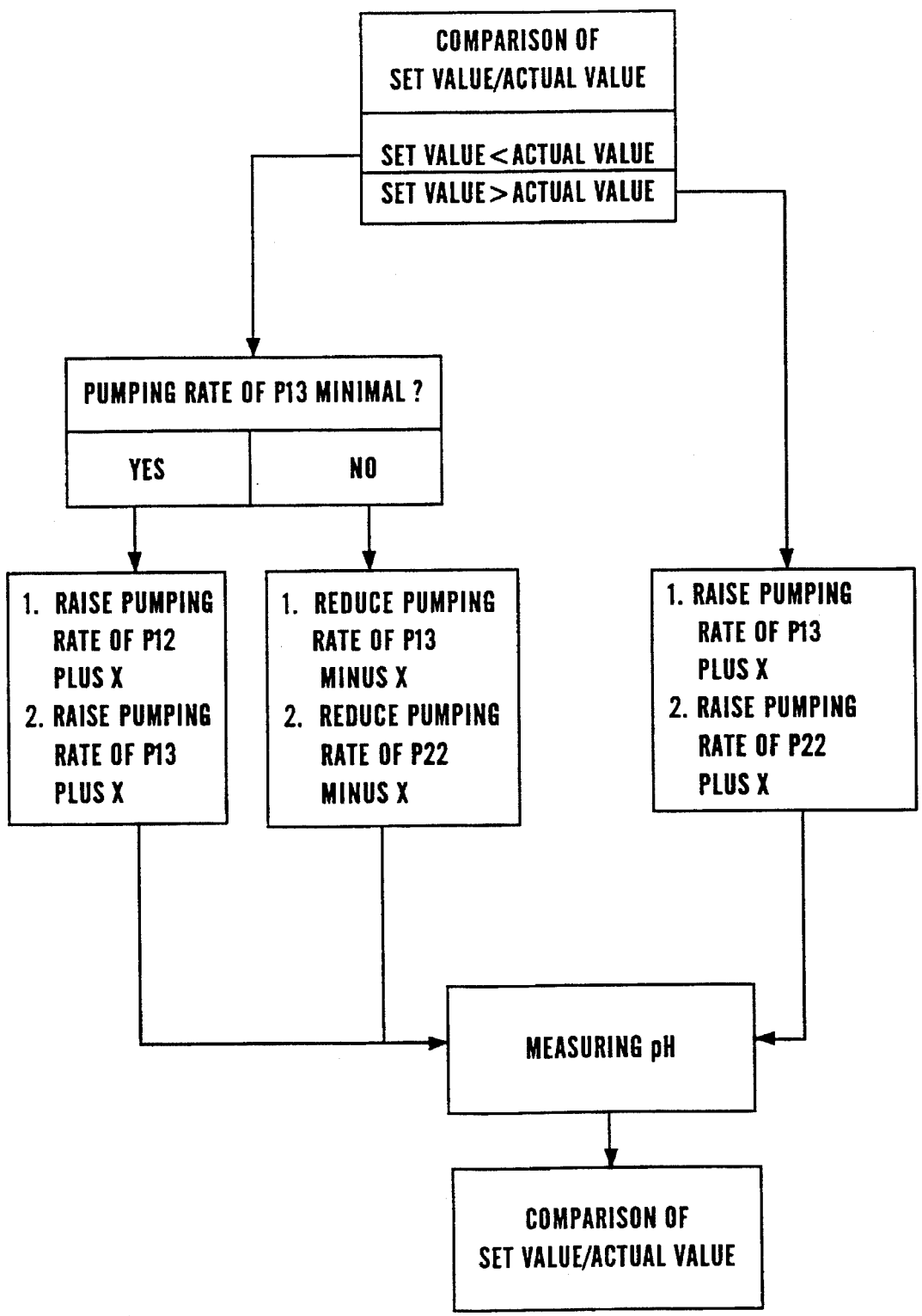
FIG. 7 shows a diagram of regulation for control of the pH value with a simplified conduct of the method.

If only a control of the pH value in solids hydrolysis is relevant and/or for reasons of organization the outlay for plant and control systems is to be reduced, it is possible for the conduct of the method and the control thereof to be simplified (see FIG. 6 and FIG. 7). This conduct of the method renders possible an exact control of the pH value during solids hydrolysis and in a manner dependent on the mixing effect in solids hydrolysis and also control of its solids content.

DETAILED ACCOUNT OF FURTHER EMBODIMENT OF THE INVENTION.

In accordance with a further preferred working embodiment the acidified mixture 12 is accordingly completely fed to the solids hydrolysis stage. A corresponding volume of mixture 13 is passed from the reactor 2 to the methanization stage. Excess mixture from the methanization stage 15 is supplied to a solids/liquid separation stage (FFT6) and residual materials 16 and furthermore excess water 23 are separately drawn off from the process.

This further, simplified working embodiment hence takes place in three stages. The solids containing substrate is acidified in a reactor 1 and the resulting acidified mixture is supplied to a reactor 2 for hydrolysis and the hydrolyzed mixture is then fed to a reactor 3 in which methanization takes place. It is only the methanized mixture which is preferentially passed to a solids/liquid separation stage. There is no solids/liquid separation stage between the reactors 1 and 2 and the reactors 2 and 3.

In this working embodiment the separating devices FFT 4 and FFT 5 are not present, that is to say a solids/liquid mixture is transferred into the reactor 2 and thence into the reactor 3. It is only the methanized mixture from the reactor 3 which is preferentially separated into a solids fraction and a liquid fraction.

This simplified working embodiment of the invention also renders possible a control of pH value, that is to say the pH values in reactors 2 and 3 may be controlled by the automatic control elements P12, P13 and P22 (see FIG. 7).

As regards details the pH value control is implemented as follows:

If owing to the quantity of supplied acids or acids formed in the reactor 2 the pH value in the reactor goes below the optimum level, then additionally a mixture from the solids hydrolysis stage 13 is supplied for methanization and a corresponding volume of methanization mixture 22 is returned back into the solids hydrolysis stage. This means that methanogenic, that is to say acid utilizing microorganisms, and buffer capacity are made available for solids hydrolysis. Accordingly there is an increase in the pH value in reactor 2.

If there is an excessive increase in reactor 2, the rate of pumping the mixture from the methanization stage into the solids hydrolysis stage 22 is reduced. There is furthermore an equal reduction in the mixture pumping rate into the methanization stage 13. If the pumping rate of P22 is zero and the pH value is still too high in reactor 2, the rate of pumping of acidified mixture to the solids hydrolysis stage P12 is increased. A diagram for automatic control in such simplified conduct of the method is to be seen in FIG. 7.

The solids content during solids hydrolysis is controlled by the degree of mixing in the reactor (complete or incomplete) and sedimentation or, respectively, floatation of the solids. The lowest solids content in reactor 2 occurs when there is a complete mixing effect. If the formation of a sludge bed or of a floating covering layer is permitted, it is possible for the mean solids concentration in the reactor to be increased. The thicker the sludge bed or the floating layer, the higher the mean solids concentration in the reactor. The thickness of the sludge bed or of the floating layer is controlled by the intensity of mixing.

The apparatus for simplified conduct of the method is to be seen from FIG. 6.

This apparatus essentially comprises a first reactor 1 for the acidification of the organic substances, a second reactor 2 for the solids hydrolysis of the slightly acidified organic substances and a reactor 3 for the methanization of the organic substances.

The reactor 1 has an inlet 10 via which the reactor is charged with the organic substances to be processed.

The reactor 1 is connected with the reactor 2 by means of a communicating element 12, which may comprise a duct, a channel or the like.

The reactor 2 is furthermore connected through the communicating element 13 with the reactor 3. The reactor 3 is in turn connected with the reactor 2 by means of the communicating element 22. Via control elements (P12, P13 and P22) the supply or return of the dissolved or undissolved substances and hence the pH value as well and the pH value in the reactor 2 and in reactor 3 are controlled.

Via the solids/liquid separating device 6, which is connected by the communicating element 15 with the reactor 3, the methanization output material is separated into the solids and the liquid excess water.

The reactors 2 and 3 furthermore have draw off elements 30 and 31 for the removal of gases.

The method in accordance with the invention and the apparatus in accordance with the invention render possible, for example, both thermophilic operation and also mesophilic operation, in which respect for instance reactors with intensive mixing or other reactors known to those in the art may be utilized.

Figure 2:
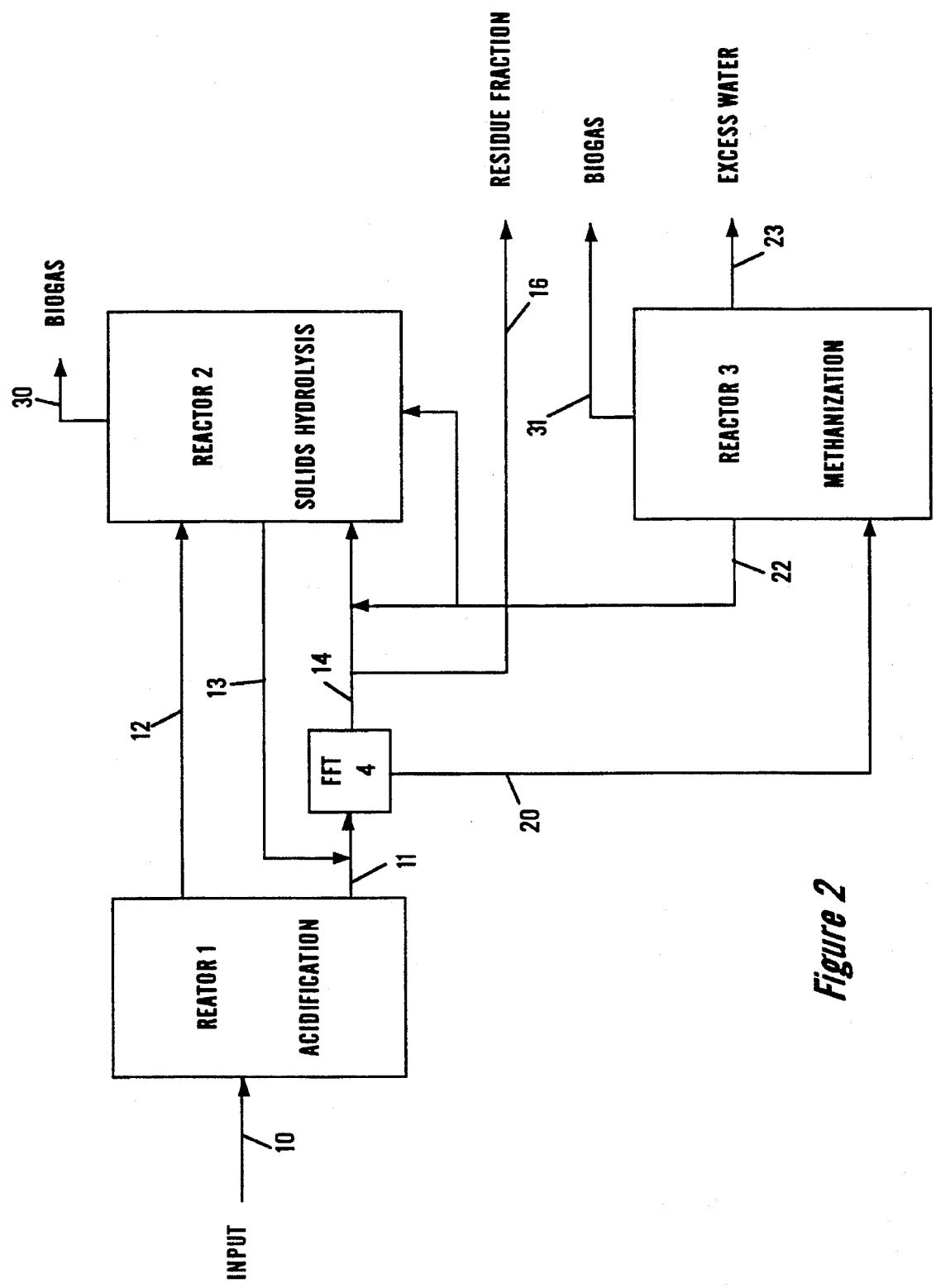
FIG. 2 is a block diagram of an apparatus for performing the method in the case of discontinuous charging of the solids hydrolysis stage, with pH value control.
Figure 3:
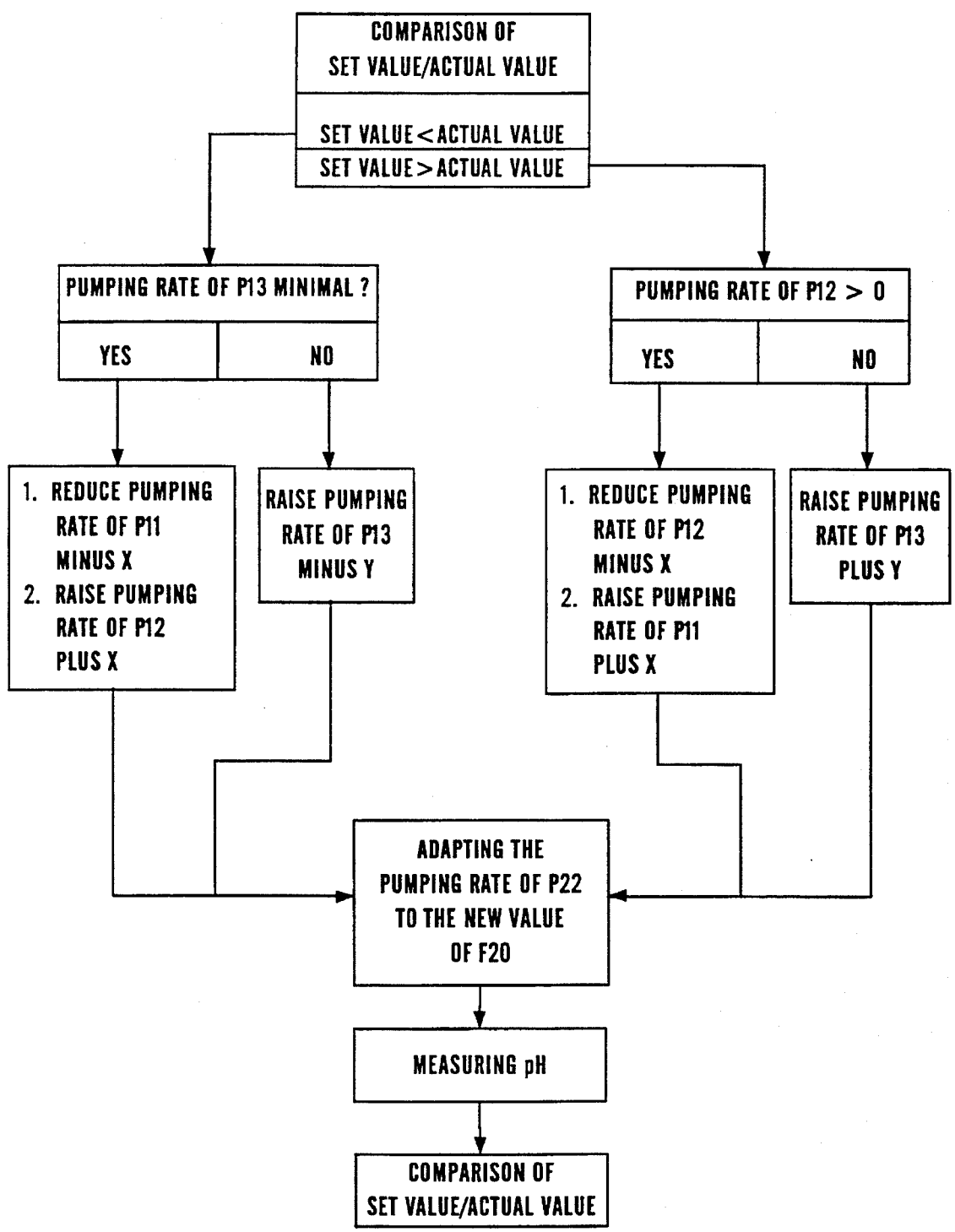
FIG. 3 is a diagram of the regulation means for pH value control in accordance with the invention.
Figure 4:
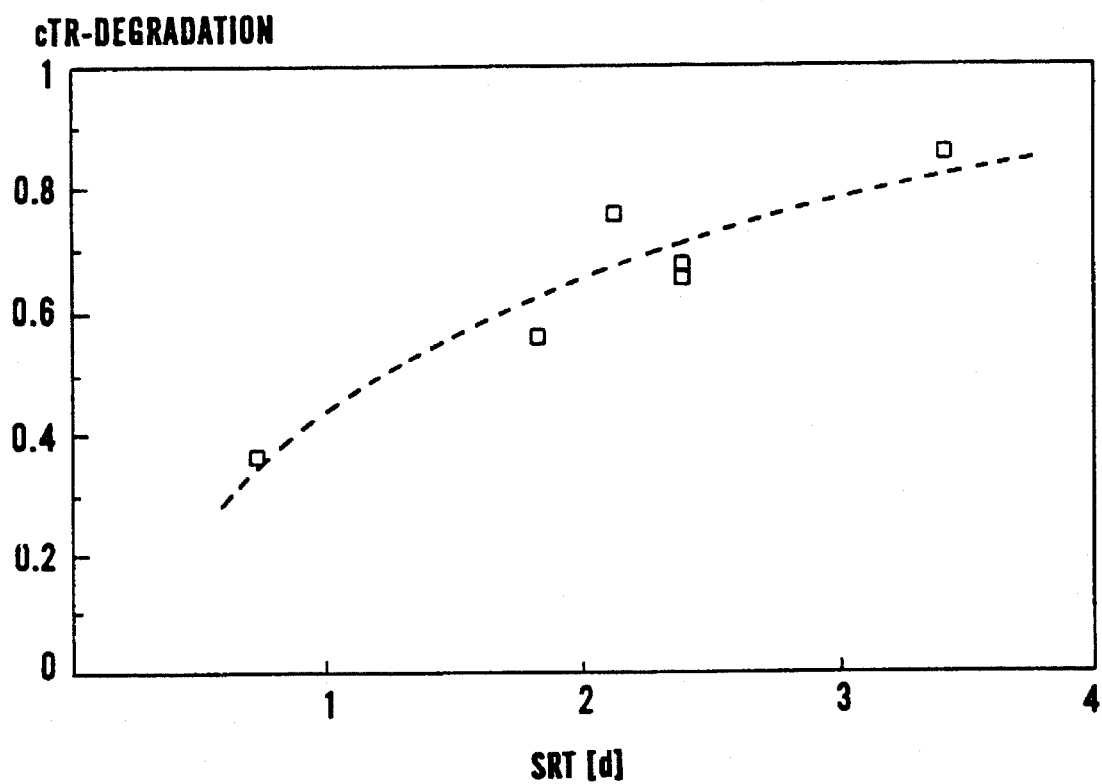
FIG. 4 shows the degree of degradation as a function of the residence time in the reactor for solids hydrolysis.
Figure 5:
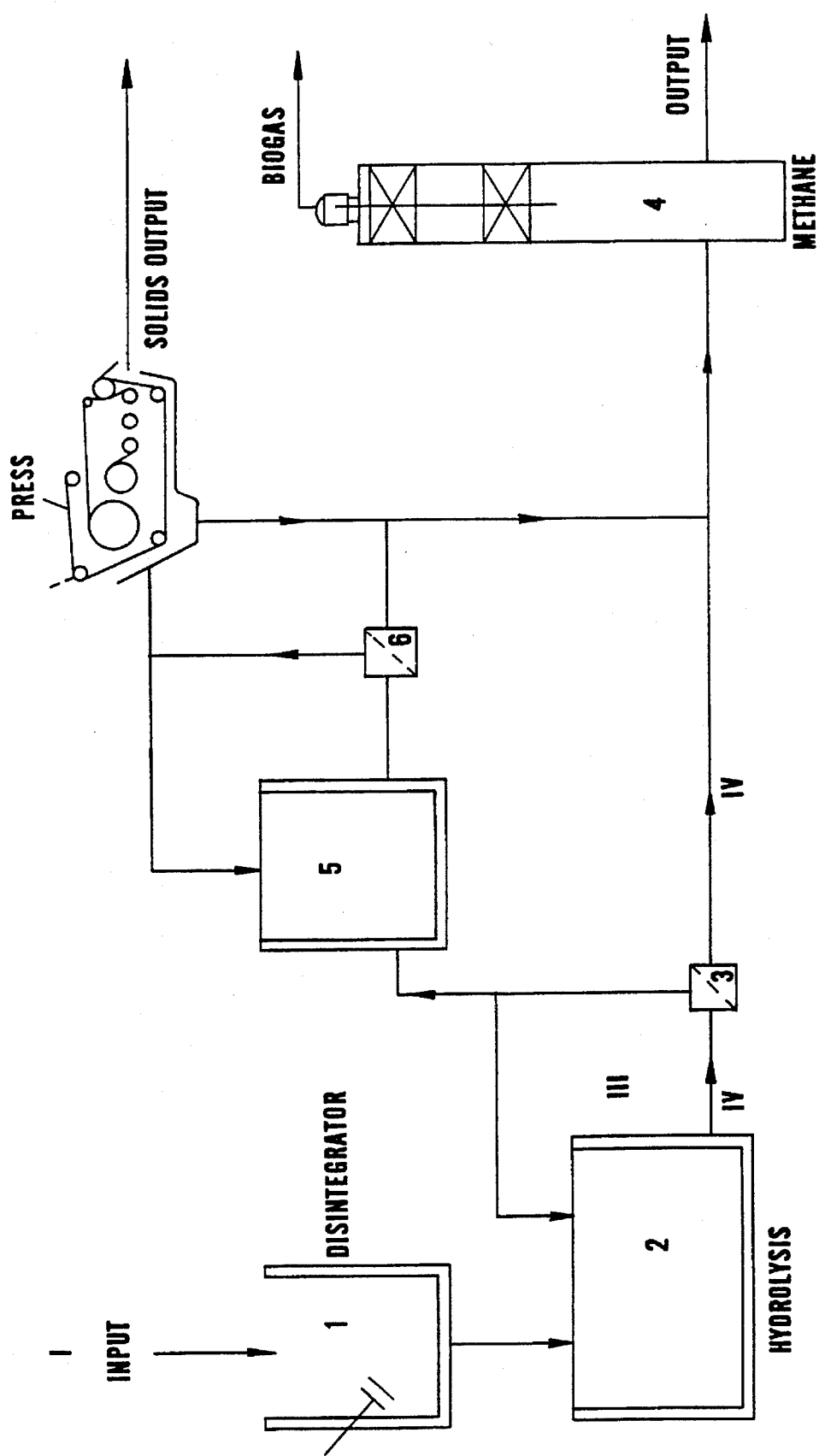
FIG. 5 shows the PAQUES method in accordance with prior art.

The simplified method described in conjunction with FIGS. 6 and 7 has the following advantages over the PAQUES method and the method described in conjunction with FIGS. 1 through 3, that is to say:

In the process no mechanical solids/liquid separation is necessary, which is extremely problematical with many substrates; either the throughput of the plant is too low or the retention of solids is insufficient or the operational costs are too high owing to the use of adjuvants.

In the described methods all three reactors may be designed as reactors with full or intensive mixing. Such reactors are not subject to deposition of lime or scale. In the case of thermophilic operation the hygienization stage is omitted. The control system is significantly less complex.

I claim:

1. A method for the anaerobic biological processing of organic substances, with pH value control, said method using separate acidification and hydrolysis steps and comprising:

supplying to a first reactor dissolved and/or undissolved organic substances and subjecting said organic substances to at least a slight acidification in said reactor;

supplying to a second reactor a major portion of the undissolved, at least partly acidified organic substances from the first reactor and performing at least one solids hydrolysis step, wherein there is no return of solids into the first reactor;

supplying to a third reactor a major portion of the dissolved, at least partly acidified organic substances from the first reactor and from the second reactor and performing at least one methanization step; and controlling a pH value in said second reactor without the addition of chemicals by at least one step selected from the group consisting of (i) adjusting the flow of organic substances from the first reactor into the second and third reactors, and (ii) adjusting the flow of organic substances from the second reactor into the third reactor.

2. The method as claimed in claim 1, wherein a major part of the organic substances from the first reactor is subjected to separation into a solids fractions, which essentially consists of the undissolved organic substances, and into a liquid fraction, which essentially consists of the dissolved organic substances.

3. The method as claimed in 1, wherein dissolved and undissolved substances are taken from the first reactor and supplied to the second reactor for pH value control to reduce the pH value.

4. The method as claimed in claim 1, wherein dissolved and undissolved substances are taken from the second reactor and from them at least a part of the dissolved organic substances is supplied to the third reactor for pH value control to increase the pH value in the second reactor; the remaining part of the drawn off organic substances being returned to the second reactor.

5. The method as claimed in claim 1, wherein the buffer capacity of the second reactor is increased and the solids content in the second reactor is controlled by removing a low solids feed from the third reactor and supplying it to the second reactor.

6. The method as claimed in claim 1, wherein the pH value control is performed using one member selected from:
   a servo member for regulating the flow between said first and second reactor;
   a servo member for regulating the flow between said first reactor and a solid/liquid separation unit located between said first and second reactor; and
   a servo member for regulating the flow between said second reactor and the solid/liquid separation unit or a combination thereof.

7. The method as claimed in claim 1, wherein excess water is taken from the third reactor and in this manner the ratio between the water supplied to the first reactor with the organic substances and the water taken from the second and third reactor is compensated for.

8. The method as claimed in claim 1, wherein in the second reactor in addition to solids hydrolysis methanization is performed and biogas comprising methane is removed from the second reactor and the third reactor.

9. The method as claimed in claim 1, wherein the first reactor is continuously or discontinuously charged with organic substances; and dissolved organic substances are continuously supplied from the second reactor to the third reactor; and residual substances are continuously removed from the second reactor, the residual substances being obtained by separation of the undissolved organic substances from the dissolved organic substances after removal from the second reactor prior to charging the third reactor with the dissolved organic substances.

10. The method as claimed in claim 1, wherein the first reactor is continuously or discontinuously charged with organic substances; and the second reactor is discontinuously charged; and residual substances are discontinuously removed from the second reactor.

11. The method as claimed in claim 1, wherein for reduction of the pH value the following steps are performed:
   a) return of the content of the reactor to the solids/liquid separation stage by reduction of the pumping rate of the servo member provided for regulating the flow between said second reactor and the solid/liquid separation unit;
   b) return of methanization output material to the reactor in accordance with the predetermined ratio;
   c) and by the steps a) and b) the solids content in the second reactor is maintained constant with the result that the pH value reducing effect is increased.

12. The method as claimed in claim 1, wherein when the pumping rate of the servo member provided for regulating the flow between said second reactor and the solid/liquid separation unit is at a minimum or zero the following steps are performed for further reduction of the pH value:
   a) acidified mixture is supplied directly to said second reactor,
   b) the supply from the servo member provided for regulating the flow between said first reactor and a solid/liquid separation unit located between said first and second reactor is reduced,
   c) the pumping rate of the servo member provided for regulating the flow between said first and second reactor is increased,
   d) the rate of the servo member provided for regulating the flow between said first reactor and a solid/liquid separation unit located between said first and second reactor is correspondingly reduced, and
   e) by adaptation of the pumping rate of a servo member provided for regulating the flow between said third and second reactor to the liquid phase produced in accordance with the predetermined ratio, the solids content in the reactor is maintained constant.

13. The method as claimed in claim 1 wherein for increasing the pH value the following steps are performed:
   a) the supply of the acidified mixture via a servo member provided for regulating the flow between said first reactor and a solid/liquid separation unit located between said first and second reactor is increased and the supply of the servo member provided for regulating the flow between said first and second reactor is correspondingly lowered;
   b) the pumping rate of the servo member provided for regulating the flow between said first reactor and a solid/liquid separation unit located between said first and second reactor is increased and the rate of the servo member provided for regulating the flow between said first and second reactor is correspondingly reduced; and
   c) the supply of methanization output material is correspondingly increased in order to maintain the solids concentration in said reactor constant.

14. The method as claimed in claim 1, wherein for further increasing the pH value the following steps are performed:
   a) the pumping rate of the servo member provided for regulating the flow between said second reactor and a solid/liquid separation unit and a servo member provided for regulating the flow between said third and second reactor via the ducts is increased;
   b) the return of the methanization output material is adapted to the quantity of filtrate produced; and
   c) through the use of steps a) and b) the solids concentration in said second reactor is maintained constant.

15. A method for the anaerobic biological processing of organic substances, with pH value control, said method using separate acidification and hydrolysis steps and comprising:
   supplying to a first reactor dissolved and/or undissolved organic substances and subjecting said organic substances to at least a slight acidification in said reactor;
   supplying to a second reactor essentially all of the undissolved, at least partly acidified organic substances from the first reactor and performing at least one solids hydrolysis step, wherein there is no return of solids into the first reactor;
   supplying to a third reactor substantially all of the at least partly hydrolyzed mixture taken from the second reactor containing solid and liquid components and performing at least one methanization step; and controlling a pH value in said second reactor without the addition of chemicals by a step selected from the group consisting of (i) adjusting the flow of organic substances from the first reactor into the second reactor and from the second reactor into the third reactor, and (ii) adjusting the flow of organic substances from the second reactor into the third reactor and from the third reactor into the second reactor.

16. The method as claimed in claim 15, wherein excess mixture from the methanization step is supplied to a solids/liquid separating device with the result that the residual materials and excess water are drawn off separately from the process.

17. The method as claimed in claim 15, wherein the pH value control is performed using one of the following servo members:

the servo member provided for regulating the flow between said first and second reactor;

the servo member provided for regulating the flow between said second and third reactor; and the servo member provided for regulating the flow between said third and second reactor or a combination thereof.

18. The method as claimed in claim 15, wherein for increasing the pH value in the second reactor the following steps are performed:

a) removal of additional mixture from the solids hydrolysis stage into the third reactor; and b) return of a corresponding quantity of methanized mixture into the second reactor.

19. The method as claimed in claim 15, wherein for reduction of the pH value in the second reactor the following steps are performed:

a) reduction of the quantity of the mixture removed from the third reactor and supplied into the second reactor; and b) a corresponding reduction of the quantity of mixture taken from the second reactor and supplied in to the third reactor.

20. The method as claimed in claim 15, wherein for further reduction of the pH value in the second reactor the pumping rate for the acidified mixture into the second reactor is increased.

21. The method as claimed in claim 15, wherein the solids content is controlled via the degree of mixing in the first and/or second reactor and a) in the case of complete mixing the solids content may be reduced or b) in the case of a reduction in mixing the solids content may be increased.

22. The method as claimed in claim 15, wherein in the second reactor in addition to solids hydrolysis methanization is performed and biogas comprising methane is removed from the second reactor and the third reactor.

23. An apparatus for the anaerobic biological processing of organic substances, with pH value control, comprising:

a first reactor provided with a supply means;

a second reactor connected to the first reactor;

a third reactor connected to the second reactor via communicating elements; and servo members for adjusting the flow of the organic substances from the first reactor into the second reactor and from the second reactor into the third reactor, or from the second reactor into the third reactor and from the third reactor into the second reactor, respectively, to control a pH value in the second reactor without the addition of chemicals, wherein there is no element for return of solids into the first reactor.

24. The apparatus as claimed in claim 23, further comprising a solids/liquid separating device wherein the third reactor is connected via a communicating element with the solids/liquid separating device.

25. The apparatus as claimed in claim 23, wherein pH value control is performed using one of the following servo members:

the servo member provided for regulating the flow between said first and second reactor;

the servo member provided for regulating the flow between said second and third reactor; and the servo member provided for regulating the flow between said third and second reactor or a combination thereof.

26. The apparatus as claimed in claim 23, further comprising outlets on the second and third reactors for the removal of gases.

27. The apparatus as claimed in 23, wherein one or more of the first, second and third reactors are adapted for full mixing of the contents thereof or is a plug-flow reactor.

28. The apparatus as claimed in claim 23, wherein the third reactor is a fixed bed reactor.

29. The apparatus as claimed in claim 23, wherein one or more of the first, second and third reactors are arranged in cascade.

30. An apparatus for the anaerobic biological processing of organic substances, with pH value control, comprising:

a first reactor having a supply means;

a second reactor connected to the first reactor via communicating elements;

a third reactor connected to the first reactor via communicating elements; and at least two servo members for adjusting the flow of the organic substances from the first reactor into the second and third reactors, or from the second reactor into the third reactor, to control a pH value in the second reactor without the addition of chemicals, wherein there is no element for return of solids into the first reactor.

31. The apparatus as claimed in claim 30, wherein the communicating elements connecting the first reactor with the second and the third reactors are connected via a separating device for the separation of dissolved and undissolved materials into a solids fraction and a liquid fraction.

32. The apparatus as claimed in claim 30, wherein the first reactor is connected via a further communicating element with the second reactor.

33. The apparatus as claimed in claim 30, wherein the second reactor is connected via a further communicating element with the element.

34. The apparatus as claimed in claim 30, wherein the third reactor is connected via a further communicating element with the second reactor directly and/or via the element.

35. The apparatus as claimed in claim 30, further comprising an outlet provided on the third reactor for the removal of water.

36. The apparatus as claimed in claim 30, wherein the second reactor is connected via a communicating element with a separating device for the separation of dissolved and undissolved materials into a solids fraction and a liquid fraction, the separating device being connected with the outlet for the liquid fraction via a communicating element and/or the element is connected with the third reactor and has an outlet for solids.

37. The apparatus as claimed in claim 30, further comprising outlets provided on the second and third reactors for the removal of gases.

38. The apparatus as claimed in claim 30, wherein one or more of the first, second and third reactors are adapted for full mixing of the contents thereof or is a plug-flow reactor.

39. The apparatus as claimed in claim 30, wherein the third reactor is a fixed bed reactor.

40. The apparatus as claimed in claim 30, wherein one or more of the first, second and third reactors are connected in cascade.

41. The apparatus as claimed in claim 30, comprising one of the following servo members:

the servo member provided for regulating the flow between said first reactor and the solid/liquid separation unit;

the servo member provided for regulating the flow between said second and said solid/liquid separation unit; and the servo member provided for regulating the flow between said first and second reactor for pH value control, or a combination thereof.

* * * * *